United States Patent [19]
Gosch et al.

[11] Patent Number: 4,982,018
[45] Date of Patent: Jan. 1, 1991

[54] REMOVAL OF CYCLOHEXANOL FROM AQUEOUS SOLUTIONS CONTAINING IT AND AROMATIC SULFONIC ACIDS

[75] Inventors: Hans-Juergen Gosch, Bad Duerkheim; Rolf Fischer, Heidelberg; Hermann Luyken, Ludwigshafen, all of Fed. Rep. of Germany

[73] Assignee: BASF Aktiengesellschaft, Ludwigshafen, Fed. Rep. of Germany

[21] Appl. No.: 400,530

[22] Filed: Aug. 30, 1989

[30] Foreign Application Priority Data

Sep. 1, 1988 [DE] Fed. Rep. of Germany .... 3829709

[51] Int. Cl.$^5$ ........................ C07C 35/08; C07C 29/74
[52] U.S. Cl. ...................................... 568/835; 568/810; 568/832
[58] Field of Search ............... 568/810, 856, 868, 835, 568/832

[56] References Cited

U.S. PATENT DOCUMENTS

| | | | |
|---|---|---|---|
| 2,044,414 | 6/1936 | Wilkinson | 568/899 |
| 3,380,971 | 4/1968 | Chalmers et al. | 260/78.5 |
| 4,003,952 | 1/1977 | Foster et al. | 568/913 |
| 4,306,101 | 12/1981 | Slaugh et al. | 568/835 |
| 4,528,409 | 7/1985 | Mitsui et al. | 568/835 |
| 4,670,612 | 6/1987 | Shirafuji et al. | 568/899 |
| 4,691,064 | 9/1987 | Shirafuji et al. | 568/835 |
| 4,849,551 | 7/1989 | Shirafuji et al. | 568/899 |

FOREIGN PATENT DOCUMENTS

| | | | |
|---|---|---|---|
| 0206631 | 12/1986 | European Pat. Off. | 568/895 |
| 0123713 | 5/1987 | European Pat. Off. | 568/835 |
| 0285911 | 10/1988 | European Pat. Off. | 568/835 |
| 0219133 | 12/1983 | Japan | 568/835 |
| 2103033 | 5/1987 | Japan | 568/835 |

*Primary Examiner*—Werren B. Lone
*Attorney, Agent, or Firm*—Keil & Weinkauf

[57] ABSTRACT

Cyclohexanol is removed from aqueous solutions containing it and aromatic sulfonic acids, obtained by hydrating cyclohexene in aqueous solutions of aromatic sulfonic acids at elevated temperatures and subsequent removal of excess cyclohexene, by (a) feeding the aqueous solution which contains the cyclohexanol and the aromatic sulfonic acid into the upper third of a first column and from 1 to 50 parts by weight of steam per part by weight of cyclohexanol into the bottom third of the column, withdrawing at the top of the column a vapor which consists essentially of cyclohexanol, cyclohexene and water, and obtaining as a bottom product an aqueous solution of the aromatic sulfonic acid, (b) condensing the vapor which consists essentially of cyclohexanol, cyclohexene and water and
 (b1) obtaining a cyclohexanol-rich phase and
 (b2) an aqueous phase, (c) utilizing the aqueous phase (b2) for generating the steam required in stage (a) and any remainder for the hydration of cyclohexene, and (d) distilling off from the cyclohexanol-rich phase (b1) in a second column a mixture of cyclohexene and water with or without cyclohexanol as top product, leaving cyclohexanol as bottom product.

6 Claims, No Drawings

REMOVAL OF CYCLOHEXANOL FROM AQUEOUS SOLUTIONS CONTAINING IT AND AROMATIC SULFONIC ACIDS

European Patent Application No. 123,713 discloses a process wherein cyclohexanol is obtained by hydrating cyclohexene at from 50° to 200° C. in from 5 to 80% strength by weight solutions of aromatic sulfonic acids in water. To prevent corrosion, the reaction is carried out for example in the presence of heteropoly acids, salts or oxides of molybdenum, tungsten or vanadium. The cyclohexanol formed by hydration of cyclohexene predominantly dissolves in the aqueous phase, which contains the aromatic sulfonic acids, and is mostly not removed therefrom even by excess cyclohexene.

JP-A2-103,033/1987 recommends aliphatic, cycloaliphatic and aromatic hydrocarbons for extracting cyclohexanol from aqueous solutions of aromatic sulfonic acids. However, appreciable amounts of extractants are necessary to obtain effective extraction. Industrially, this is very expensive.

In another process known from Japanese Patent Application No. 16,125/1968, cyclohexanol is initially separated from the aqueous solution containing it and aromatic sulfonic acids by steam distillation and extracted with ether from the aqueous distillate obtained and then isolated by evaporation of the solvent. Apart from the fact that it is again necessary to use solvents for the extraction, a not inconsiderable portion of the cyclohexanol is converted back into cyclohexene during the steam distillation. For this reason an attempt was made in this prior art to dilute the aqueous starting solution which contains cyclohexanol and aromatic sulfonic acids to an appreciable extent in order to reduce the backformation to cyclohexene. However, this has the disadvantage that the aqueous solution of aromatic sulfonic acids thus obtained can no longer be used for the hydration without prior concentrating.

It is an object of the present invention to provide a process for removing cyclohexanol from aqueous solutions containing it and aromatic sulfonic acids where no extractant is required, the backformation of cyclohexanol to cyclohexene is kept to a minimum and an aqueous solution of aromatic sulfonic acids which is directly utilizable for the hydration of cyclohexene is obtained, and where, furthermore, no waste waters in need of treatment are produced.

We have found that this object is achieved by a process for removing cyclohexanol from an aqueous solution containing it and an aromatic sulfonic acid, which has been obtained by hydrating cyclohexene in an aqueous solution of an aromatic sulfonic acid at an elevated temperature and subsequent removal of excess cyclohexene, by steam distillation, which comprises (a) feeding the aqueous solution which contains the cyclohexanol and the aromatic sulfonic acid into the upper third of a first column and from 1 to 50 parts by weight of steam per part by weight of cyclohexanol into the bottom third of the column, withdrawing at the top of the column a vapor which consists essentially of cyclohexanol, cyclohexene and water, and obtaining as a bottom product an aqueous solution of the aromatic sulfonic acid, (b) condensing the vapor which consists essentially of cyclohexanol, cyclohexene and water and
 (b1) obtaining a cyclohexanol-rich phase and
 (b2) an aqueous phase, (c) utilizing the aqueous phase (b2) for generating the steam required in stage a and any remainder for the hydration of cyclohexene, and (d) separating from the cyclohexanol-rich phase (b1) in a second column a mixture of cyclohexene and water with or without cyclohexanol as top product and cyclohexanol as bottom product.

The novel process has the advantage that the use of solvents for the extraction is avoided. Furthermore, the novel process has the advantage that the backformation of cyclohexanol to cyclohexene is minimized. It has the further advantage that the aqueous solution of aromatic sulfonic acids obtained is reusable for the hydration of cyclohexene without prior concentrating. In addition, no waste waters in need of treatment are produced.

According to the invention, the starting point is an aqueous solution which contains cyclohexanol and an aromatic sulfonic acid in solution. A solution of this type is obtained in the hydration of cyclohexene to cyclohexanol by reacting cyclohexene in an aqueous solution which contains from 5 to 80% by weight of an aromatic sulfonic acid, in particular a benzene- or naphthalene-sulfonic acid, which may be substituted, such as benzenesulfonic acid, toluenesulfonic acid or naphthalenesulfonic acid, or dodecylbenzenesulfonic acid, at, for example, from 50° to 200° C., in particular from 70° to 150° C., advantageously under from 1 to 10 bar. It is advantageous to use in addition molybdenic acid or a salt thereof, vanadium oxide or a vanadate in an amount of for example from 0.001 to 5% by weight, based on the aromatic sulfonic acid. In addition, it is also advisable to use a heteropoly acid such as phosphorusmolybdenic acid, phosphorustungstic acid, phosphorusmolybdenictungstic acid or phosphorusmolybdenicvanadic acid. Suitable processes are described for example in European Patent No. 123,713 and European Patent Application No. 206,631. Other starting materials besides cyclohexene are cyclohexene-containing hydrocarbon mixtures, for example mixtures of cyclohexene and cyclohexane or cyclohexene, cyclohexane and benzene. The reaction mixture obtained in the course of the hydration separates into an organic phase comprising excess cyclohexene with or without cyclohexane and benzene, this phase also containing minor amounts of cyclohexanol and any by-products which appear, and, after the organic phase has been separated off, an aqueous phase from which the cyclohexanol needs to be separated. A typical composition of the aqueous phase obtained is for example from 5 to 10% by weight of cyclohexanol, from 40 to 70% by weight of aromatic sulfonic acid and from 20 to 50% by weight of water.

According to the invention, the aqueous solution which contains the cyclohexanol and the aromatic sulfonic acid is steam distilled in a first column. To this end, the aqueous solution of cyclohexanol and aromatic sulfonic acid is fed into the upper third of the first column and the steam into the lower third of the column. Per part by weight of cyclohexanol from 1 to 50 parts by weight of steam, in particular from 4 to 15 parts by weight of steam, are fed in. Suitable columns are for example packed columns, bubble cap plate columns, valve plate columns and sieve plate columns. The columns advantageously have from 1 to 50, in particular from 1 to 5, theoretical plates. It is particularly useful to keep the cyclohexanol in the column for a short residence time, for example from 1 to 60 minutes.

The cyclohexanol is in general separated off at from 50° to 170° C., in particular from 90° to 110° C. This is done in general under atmospheric pressure. However, it is also possible to carry out the distillation under reduced pressure, for example down to 20 mbar, or under superatmospheric pressure, for example at up to 10 bar.

At the top of the column a vapor is withdrawn consisting essentially of cyclohexanol, cyclohexene and water. At the base of the column an aqueous solution of aromatic sulfonic acid is obtained.

In stage b, the vapor obtained at the top of column 1, which consists essentially of cyclohexanol, cyclohexene and water, is condensed to give a cyclohexanol-rich phase (b1) which consists essentially of cyclohexanol, water and cyclohexene. A typical composition is for example from 50 to 90% by weight of cyclohexanol, from 0.1 to 10% by weight of cyclohexene and from 12 to 15% by weight of water plus small amounts of impurities. An aqueous phase (b2) is also obtained. It has a typical composition of for example from 93 to 97% by weight of water and from 3 to 7% by weight of cyclohexanol.

Advantageously, the vapor is compressed, for example to a pressure of 1.5 bar, prior to being condensed, and in the condensation the thermal energy is used in stage c as described hereinafter or in some other way.

In stage c, sufficient of the aqueous phase (b2) is evaporated, advantageously by heat exchange with the compressed vapor of stage b, as corresponds to the amount of steam required for the first column of stage a. The remainder of aqueous phase (b2) is reused for the hydration of cyclohexene, optionally together with the bottom product of stage a.

The cyclohexanol-rich phase (b1) is separated in stage d in a second column into a mixture of cyclohexene and water with or without cyclohexanol as top product and cyclohexanol as bottom product. Suitable columns are for example packed columns, sieve plate columns, bubble cap plate columns and valve plate columns. These columns advantageously have from 5 to 50, in particular from 10 to 25, theoretical plates. The top of the column is advantageously maintained at from 40° to 150° C., and the base of the column at from 80° to 200° C. In general, the distillation is carried out under atmospheric pressure. However, it is also possible to employ reduced pressure, for example down to 10 mbar, or superatmospheric pressure, for example up to 5 bar. Advantageously, the cyclohexanol-rich phase (b1) is fed into the middle portion of the column. The vapor obtained at the top of the column is condensed and separates into a cyclohexene phase (d1) which contains water with or without cyclohexanol and which is for example recycled into the hydration and an aqueous phase (d2) which contains cyclohexene with or without cyclohexanol and which is advantageously recombined with the phase (b2) and/or directly recycled into the hydration stage. The bottom product obtained at the base of the column is cyclohexanol with a purity of for example from 99 to 100% by weight.

It is particularly advantageous to withdraw from the side of the second column, for example from its middle third, a gaseous or liquid stream which separates into two phases, a cyclohexanol-rich phase (d3) having a typical composition of from 50 to 90% by weight of cyclohexanol, from 0 to 40% by weight of cyclohexene and from 1 to 20% by weight of water, which is recycled back into the second column, and an aqueous phase (d4) which consists essentially of water and from 0.1 to 7% by weight of cyclohexanol, which is advantageously combined with the phase (b2) of the condensate of the first column, if the water is required for steam generation, and/or directly recycled into the hydration stage, optionally together with the bottom product of the first column.

EXAMPLE 1

(1a) Removal of Cyclohexanol by Steam Distillation 480 g/h of a solution of 10 parts by weight of cyclohexanol, 53 parts by weight of p-toluenesulfonic acid, 2 parts by weight of molybdatophosphoric acid and 35 parts by weight of water were continuously fed onto the top plate of a heatable three-plate bubble cap plate column having a plate diameter of 50 mm. At the same time, 580 g/h of steam were introduced above the base of the column. The weight ratio of cyclohexanol:steam was thus 1:12. The column was heated in such a way that the internal temperature was 108° C. Under these conditions, the top product was 600 g/h of distillate. The distillate was composed of 30 g/h of a cyclohexanol-rich phase and 570 g/h of an aqueous phase. The cyclohexanol-rich phase comprised 83.6% by weight of cyclohexanol, 3.3% by weight of cyclohexene and 13.1% by weight of water. The aqueous phase contained 96% by weight of water and 3.7% by weight of cyclohexanol. The distillates thus contained 46 g/h of cyclohexanol and 0.9 g/h of cyclohexene. The bottom product was 460 g/h of an aqueous sulfonic acid solution composed of 56% by weight of p-toluenesulfonic acid, 42% by weight of water, 2% by weight of molybdatophosphoric acid and 0.2% by weight of cyclohexanol. Hence, 96 mol % of the cyclohexanol present in the sulfonic acid solution were separated off successfully; only 2 mol % were converted back into cyclohexene.

(1b) Isolation of Pure Cyclohexanol

To isolate pure cyclohexanol, a heatable bubble cap plate column having a plate diameter of 50 mm and comprising 30 bubble cap plates was used. 114 g of the cyclohexanol-rich phase passing over at the top by the steam distillation of Example (1a) (83.6% of cyclohexanol, 13.1% of water, 3.3% of cyclohexene) were introduced per hour onto the 16th plate of the column counting upward.

At the top of the column, the following product quantities were isolated per hour following condensation and phase separation:

3.7 g of organic phase (reflux ratio 6.8) comprising 99.5% of cyclohexene and 0.5% of water, recyclable into the hydration stage and 3.0 g of an aqueous phase comprising 99.8% of water and 0.2% of cyclohexene, recyclable into the hydration stage.

At the 14th plate of the column, counting upward, the entire liquid was withdrawn and separated in a phase separator. This produced per hour 132 g of an organic phase comprising 20.6% of cyclohexene, 73.6% of cyclohexanol and 5.8% of water. The organic phase was passed back in onto the 13th plate of the column. The phase separation also yielded per hour 12.3 g of an aqueous phase comprising 96.8% of water, 3.0% of cyclohexanol and 0.1% of cyclohexene. The aqueous phase can be recycled into the hydration stage.

The bottom product of the column comprised 95.2 g of cyclohexanol per hour in a purity of 99.9%.

EXAMPLES 2 TO 4

The steam distillation was carried out as described in Example 1a. The results in Table 1 show that as the amount of steam (based on cyclohexanol) decreases, the amount of cyclohexanol separated off decreases and the rate of backformation of cyclohexanol increases (ol=-cyclohexanol, ene=cyclohexene).

TABLE 1

| Example | Acid solution (g/h) | $H_2O$ vapor (g/h) | Weight ratio of ol:$H_2O$ vapor | Distillate g/h ol | ene | Bottom product g/h ol | ene | Ol cleavage (mol %) |
|---|---|---|---|---|---|---|---|---|
| 2 | 520 | 150 | 1:2.9 | 20 | 10 | 20 | 1 | 25 |
| 3 | 610 | 250 | 1:4.1 | 42 | 3 | 15 | 1 | 8 |
| 4 | 620 | 520 | 1:8.4 | 51 | 2 | 7 | 2 | 8 | ol = cyclohexanol; ene = cyclohexene

EXAMPLES 5 TO 7

The distillation was carried out as described in Example 1a, except that a heatable bubble cap plate column of 13 bubble cap plates and a plate diameter of 60 mm was used. The cyclohexanol/sulfonic acid solution was introduced at the 3rd plate from the top and the steam at the 9th plate from the top. The temperature in the column was 107° C. To remove the cyclohexanol, various ratios of cyclohexanol : steam were used. The results are given in Table 2.

TABLE 2

| Example | Acid solution (g/h) | $H_2O$ vapor (g/h) | Weight ratio of ol:$H_2O$ vapor | Distillate g/h ol | ene | Bottom product g/h ol | ene | Ol cleavage (mol %) |
|---|---|---|---|---|---|---|---|---|
| 5 | 572 | 150 | 1:2.6 | 24 | 11 | 18 | 1 | 26 |
| 6 | 600 | 470 | 1:7.8 | 52 | 4 | 2 | 1 | 10 |
| 7 | 570 | 600 | 1:10.5 | 53 | 3 | — | — | 6 |

EXAMPLES 8 TO 11

The distillation was carried out as described in Examples 5 to 7, except that the steam was introduced onto the 13th bubble cap plate, counting from the top. The temperature in the column was 108° C. The results in Table 3 show, compared with those in Table 1, that increasing the number of actual plates leads to increased cyclohexene formation and reduced cyclohexanol removal.

TABLE 3

| Example | Acid solution (g/h) | $H_2O$ vapor (g/h) | Weight ratio of ol:$H_2O$ vapor | Distillate g/h ol | ene | Bottom product g/h ol | ene | Ol cleavage (mol %) |
|---|---|---|---|---|---|---|---|---|
| 8 | 530 | 135 | 1:2.5 | 17 | 14 | 17 | 2 | 36 |
| 9 | 560 | 220 | 1:3.9 | 29 | 14 | 9 | 1 | 32 |
| 10 | 570 | 450 | 1:7.9 | 50 | 6 | — | — | 13 |
| 11 | 600 | 600 | 1:10 | 55 | 3 | — | 1 | 8 |

EXAMPLE 12

The distillation was carried out as described in Examples 9 to 11, except that the temperature in the column was 116° C. The result in Table 4 shows compared with Example 9 (Table 3) that increasing the column temperature increases the amount of cyclohexanol removed but also increases the amount of cyclohexene.

TABLE 4

| Example | Acid solution (g/h) | $H_2O$ vapor (g/h) | Weight ratio of ol:$H_2O$ vapor | Distillate g/h ol | ene | Bottom product g/h ol | ene | Ol cleavage (mol %) |
|---|---|---|---|---|---|---|---|---|
| 12 | 570 | 250 | 1:4.3 | 36 | 16 | — | 1 | 36 |

We claim:
1. A process for removing cyclohexanol from an aqueous solution containing cyclohexanol and an aromatic sulfonic acid, which solution has been obtained by hydrating cyclohexene in an aqueous solution of an aromatic sulfonic acid at an elevated temperature and subsequent removal of excess cyclohexene, which comprises

(a) feeding the aqueous solution which contains the cyclohexanol and the aromatic sulfonic acid into the upper third of a first column and from 1 to 50 parts by weight of steam per part by weight of cyclohexanol into the bottom third of the column, maintaining a temperature of from 50° to 70° C. in the column, withdrawing at the top of the column a vapor which consists essentially of cyclohexanol, cyclohexene and water, and obtaining as a bottom product an aqueous solution of the aromatic sulfonic acid, (b) condensing the vapor which consists essentially of cyclohexanol, cyclohexene and water to form (b1)

a cyclohexanel-rich phase and (b2) an aqueous phase, (c) utilizing the aqueous phase (b2) for generating the steam required in stage (a) and any remainder for the hydration of cyclohexene, and (d) distilling off from the cyclohexanol-rich phase (b1) in a second column a mixture of cyclohexene and water with or without cyclohexanol as top product, leaving cyclohexanol as bottom product.

2. A process as defined in claim 1, wherein a temperature of from 90° to 110° C. is maintained in stage a.

3. A process as defined in claim 1, wherein from 4 to 15 parts by weight of steam per part by weight of cyclohexanol are fed in at stage a.

4. A process as defined in claim 1, wherein the vapor obtained in stage a is compressed and the amount of steam required for stage a is produced by heat exchange with the aqueous phase (b2).

5. A process as defined in claim 1, wherein in stage d the cyclohexanol-rich phase is fed into the middle third of the second column, a mixture of cyclohexene and water is obtained at the top of the column, a mixture of cyclohexanol and water is withdrawn from the side of the middle third of the column, and after phase separation the cyclohexanol-rich phase is recycled back into the column and the aqueous phase is combined with the aqueous phase (b1), and cyclohexanol is obtained as bottom product.

6. A process as defined in claim 1, wherein in stage d the top of the column is maintained at from 40° to 150° C. and the base of the column is maintained from 80° to 200° C.

* * * * *